US012678579B2

(12) United States Patent　　(10) Patent No.:　US 12,678,579 B2
Gilmartin　　(45) Date of Patent:　Jul. 14, 2026

(54) INTEGRATED MULTIMODAL COLORIMETRIC BASED ASPIRATION DETECTION AND INTUBATION PLACEMENT VERIFICATION SYSTEM AND METHOD

(71) Applicant: Charles Gilmartin, San Anselmo, CA (US)

(72) Inventor: Charles Gilmartin, San Anselmo, CA (US)

( * ) Notice: Subject to any disclaimer, the term of this patent is extended or adjusted under 35 U.S.C. 154(b) by 1568 days.

(21) Appl. No.: 17/088,794

(22) Filed: Nov. 4, 2020

(65) Prior Publication Data

US 2021/0128855 A1　　May 6, 2021

Related U.S. Application Data

(60) Provisional application No. 62/930,096, filed on Nov. 4, 2019.

(51) Int. Cl.
*A61M 16/04*　　(2006.01)
(52) U.S. Cl.
CPC . *A61M 16/0411* (2014.02); *A61M 2016/0413* (2013.01); *A61M 2205/3324* (2013.01); *A61M 2205/584* (2013.01); *A61M 2230/432* (2013.01)
(58) Field of Classification Search
None
See application file for complete search history.

(56) References Cited

U.S. PATENT DOCUMENTS

| | | | | |
|---|---|---|---|---|
| 4,090,518 | A | * | 5/1978 | Elam ................. A61M 16/0484 128/207.15 |
| 4,327,720 | A | * | 5/1982 | Bronson ........... A61M 16/0459 128/911 |
| 4,351,330 | A | * | 9/1982 | Scarberry ............ A61N 1/0517 607/124 |
| 4,774,945 | A | * | 10/1988 | White .................. A61M 16/04 128/207.18 |
| 4,790,327 | A | | 12/1988 | Despotis |
| 4,821,710 | A | * | 4/1989 | Greunwald ....... A61M 16/0488 128/207.14 |
| 4,928,687 | A | | 5/1990 | Lampotang et al. |
| 4,994,117 | A | | 2/1991 | Fehder |
| 5,005,572 | A | | 4/1991 | Raemer et al. |
| 5,166,075 | A | | 11/1992 | Fehder |

(Continued)

*Primary Examiner* — LaToya M Louis

(74) *Attorney, Agent, or Firm* — Blynn L. Shideler; Krisanne Shideler; BLK Law Group

(57) ABSTRACT

An integrated multimodal colorimetric based aspiration detection and intubation placement verification system for an endotracheal tube and associated method includes a housing configured to be coupled to the endotracheal tube whereby patient exhalation can flow through an internal passage of the housing, and colorimetric based sensors within the housing and configured to come into contact with the patient exhalation, where the colorimetric based sensors are visible from the exterior of the housing, and wherein the colorimetric sensors include at least two of i) CO2 sensor, ii) a sensor for a first gastric acid, iii) a sensor for a second gastric acid different from the first gastric acid, and iv) a PH sensor. An associated method is disclosed. The integrated multimodal colorimetric based system can be used with other respiratory devices other than endotracheal tubes.

20 Claims, 2 Drawing Sheets

(56) References Cited

U.S. PATENT DOCUMENTS

| | | | | |
|---|---|---|---|---|
| 5,179,002 | A | 1/1993 | Fehder | |
| 5,846,836 | A | 12/1998 | Mallow | |
| 5,965,061 | A | 10/1999 | Larsson et al. | |
| 6,502,573 | B1 | 1/2003 | Ratner | |
| 7,178,519 | B2 * | 2/2007 | Melker | A61M 16/0488 |
| | | | | 128/207.14 |
| 7,747,319 | B2 * | 6/2010 | Freeman | A61M 16/0488 |
| | | | | 128/207.14 |
| 7,921,847 | B2 * | 4/2011 | Totz | A61M 16/04 |
| | | | | 128/207.14 |
| 8,720,445 | B2 * | 5/2014 | Cain | A61M 16/04 |
| | | | | 128/207.14 |
| 9,241,655 | B2 * | 1/2016 | Deighan | A61M 16/04 |
| 10,940,282 | B2 * | 3/2021 | Pacey | A61M 16/208 |
| 11,077,029 | B2 * | 8/2021 | Elia | A61B 5/4836 |
| 11,172,876 | B2 * | 11/2021 | Gilmartin | A61B 5/082 |
| 11,304,877 | B2 * | 4/2022 | Strawder | A61J 15/0073 |
| 2007/0017527 | A1 * | 1/2007 | Totz | A61M 16/0415 |
| | | | | 128/207.15 |
| 2007/0163596 | A1 * | 7/2007 | Mikkaichi | A61M 16/0493 |
| | | | | 128/207.14 |
| 2010/0106208 | A1 * | 4/2010 | Freeman | A61N 1/3925 |
| | | | | 607/5 |
| 2010/0179417 | A1 * | 7/2010 | Russo | A61M 39/08 |
| | | | | 604/264 |
| 2012/0204866 | A1 * | 8/2012 | Kizer | A61M 25/0102 |
| | | | | 128/200.26 |
| 2014/0137867 | A1 * | 5/2014 | Pacey | A61M 16/0488 |
| | | | | 128/207.14 |
| 2014/0333007 | A1 * | 11/2014 | Nasir | A61M 16/0409 |
| | | | | 128/207.15 |
| 2019/0167171 | A1 * | 6/2019 | Gallagher | A61B 10/0045 |
| 2019/0240115 | A1 * | 8/2019 | Elia | A61M 1/73 |
| 2019/0282160 | A1 * | 9/2019 | Gilmartin | A61B 5/742 |
| 2020/0237202 | A9 * | 7/2020 | Shields | A61B 1/07 |
| 2020/0330324 | A1 * | 10/2020 | Freeman | A61N 1/3937 |
| 2021/0346626 | A1 * | 11/2021 | Pacey | A61M 16/0488 |
| 2021/0353505 | A1 * | 11/2021 | Elia | A61M 1/73 |
| 2021/0386949 | A1 * | 12/2021 | Pacey | A61M 16/0057 |

* cited by examiner

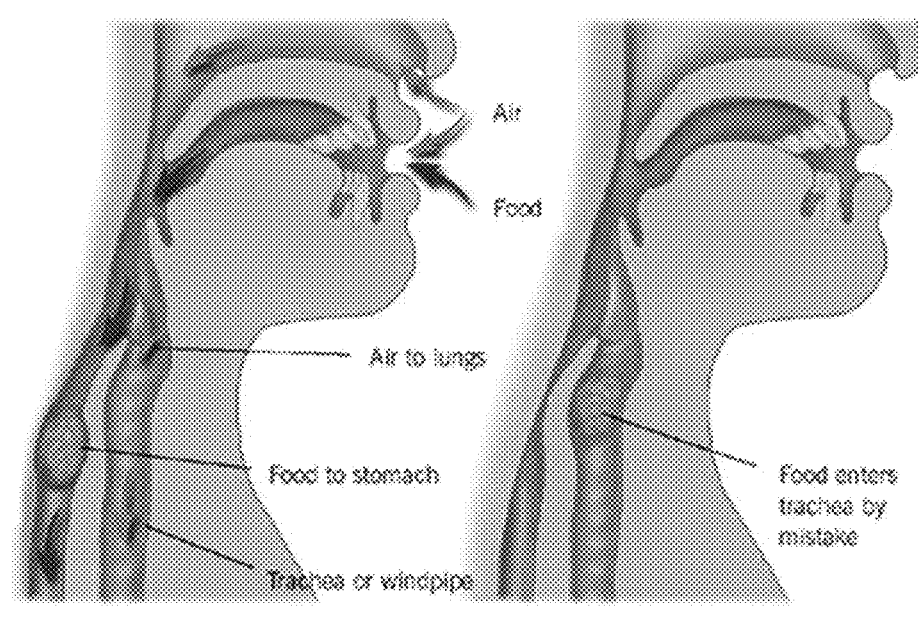
PRIOR ART
FIGURE 1A
PRIOR ART
FIGURE 1B
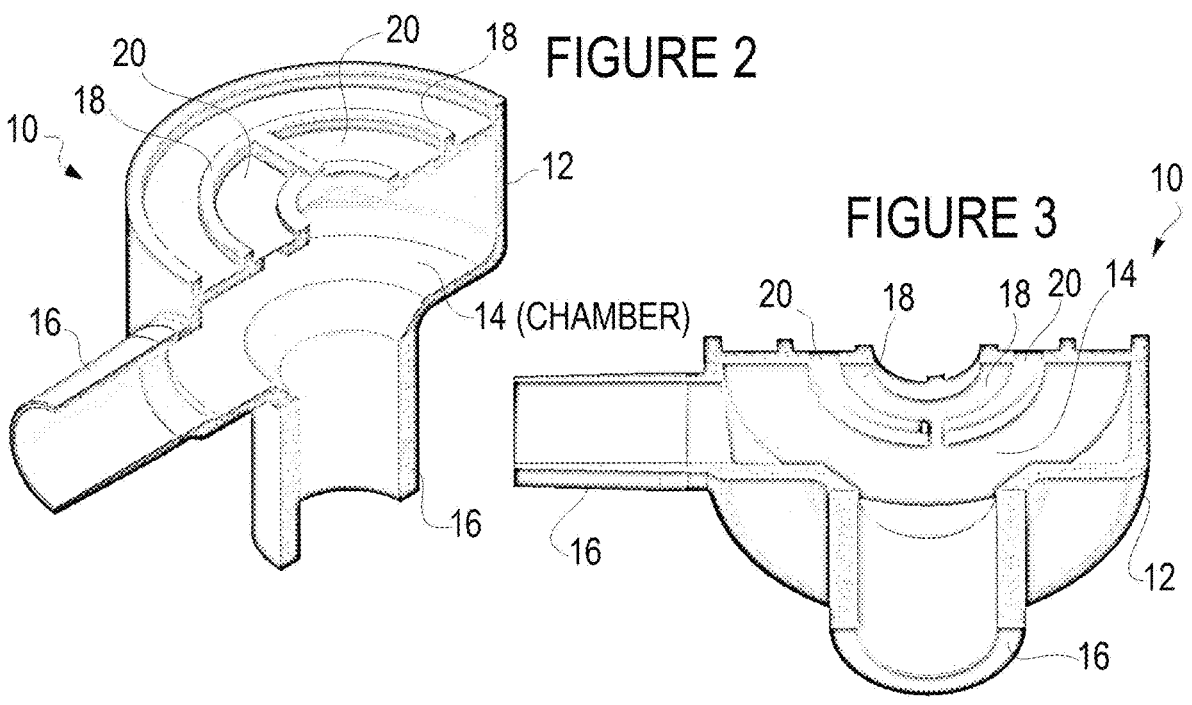
FIGURE 2
FIGURE 3

INTEGRATED MULTIMODAL COLORIMETRIC BASED ASPIRATION DETECTION AND INTUBATION PLACEMENT VERIFICATION SYSTEM AND METHOD

RELATED APPLICATIONS

This application claims priority to U.S. Patent Application Ser. No. 62/930,096 filed Nov. 4, 2019 titled "Integrated Multimodal Colormetric Based Aspiration Detection and Intubation Placement Verification System and Method".

BACKGROUND INFORMATION

1. Field of the Invention

The present invention relates to improving respiratory monitory procedures, and more broadly to a method and an apparatus for aspiration detection in respiratory assist device patients and for intubation verification of endotracheal tubes.

2. Background Information

Aspiration is generally defined as the entry of foreign material into the lungs. This can be due to inhalation of food or liquids during swallowing or due to regurgitation of stomach contents. Aspiration is schematically shown in Prior Art FIG. 1B, while FIG. 1A illustrates conventional swallowing.

Patient aspiration can lead to a number of patient complications including aspiration pneumonia and aspiration pneumonitis.

Studies have put incidence rates of aspiration pneumonia at around 5 to 15% of Community Acquired Pneumonia. See, for reference, Dibardina D M, Wunderrink R G (February 2015) "Aspiration Pneumonia: A Review of Modern Trends." *Journal of Critical Care.* 30 (1): 40-48; See also Marik P E. "Aspiration pneumonitis and aspiration pneumonia" *N Engl J Med* 2001; 344:665-71. The rate of aspirational pneumonia can be as high as 20% in nursing home acquired pneumonia, see for reference Oh E, Weintraub N, Dhanani S. "Can we prevent aspiration pneumonia in the nursing home?" *J Am Med Dir Assoc* 2005; 6 (3 Suppl):576-80, and Fein A M, "Pneumonia in the elderly. Special diagnostic and therapeutic considerations" *Med Clin North Am* 1994, 78:1015-33. Additionally, it has been estimated that aspiration pneumonia occurs in 1 in every 2-3000 patients undergoing surgery, and this rate can be 3× higher in patients undergoing thoracic surgery. It occurs frequently in patients admitted with drug overdose and exhibits higher mortality rates. See Lanspa M, Peyrani P, Wiemkwn T, Wilson E, Ramirez J, Dean N (2015), "Characteristics associated with clinician diagnosis of aspiration pneumonia; a descriptive study of afflicted patients and their outcomes". *J Hosp Med.* 10 (2): 90-6. It is the most common cause of death in patients suffering from dysphagia due to neurologic disorders, see van der Maarel-Wierink C D, Vanobbergen J N, Bronkhorst E M, Schols J M, de Baat C. "Meta-analysis of dysphagia and aspiration pneumonia in frail elders" *J Dent Res* 2011; 90:1398-404.

As alluded to above, aspiration is more common or becomes more likely with a number of conditions. For example, aspiration is more likely in the following conditions, including: difficulty swallowing (certain neurological conditions, stroke, etc.); vomiting, GERD, Placement and use of an NG tube, alcoholism, impaired consciousness, impaired cognition, seizures, use of a ventilator. See also a recent, at the time of this filing, paper by IlyaKagan, Moran Hellerman-ltzhaki, Ido Neuman, Yehuda D. Glass, Pierre Singer titled "Reflux events detected by multichannel bio-impedance smart feeding tube during high flow nasal cannula oxygen therapy and enteral feeding: First case report" Journal of Critical Care Volume 60, December 2020, Pages 226-229.

A separate complication of aspiration is aspiration pneumonitis, wherein the inhaled substances during aspiration are directly toxic to the lungs, causing chemical pneumonitis, also called Mendelson syndrome. Gastric acid, with a low pH (1.5-3.0), can cause corrosive damage to the lungs. Pneumonitis can resolve within a few days, or progress to Acute Respiratory Distress Syndrome (ARDS). There can also be a superimposed (secondary) bacterial infection in the tissue damaged by chemical pneumonitis. Aspiration pneumonitis is distinctly different from aspiration pneumonia. Aspiration pneumonitis (Mendelson's syndrome) is a chemical injury caused by the inhalation of sterile gastric contents, whereas aspiration pneumonia is an infectious process caused by the inhalation of oropharyngeal secretions that are colonized by pathogenic bacteria. Aspiration pneumonia presents with many of the same symptoms and signs as pneumonitis, but takes longer to develop. Fever caused by aspiration pneumonia is generally of a higher grade than in pneumonitis.

The applicant has been developing tools to minimize aspiration that can lead to the above complications. The applicant has developed a method of aspiration detection in respiratory assist device patients comprising the steps of: coupling an HCL sensor to one of a respiratory assist device of a patient; detecting the presence of HCL particles indicative of aspiration of the patient via a processer coupled to the HCL sensor; and displaying results for aspiration of the patient on the audio visual display. This earlier HCL sensor platform did have proposed applications in a variety of respiratory assist devices including in the nasal cannula and masks of ventilation systems and also in CPAP devices, Bipap devices and endotracheal tubes. The present invention represents continuation of this work, and can be considered an HCL platform in this same family, but the integrated sensor of the present invention is optimized for certain aspects of endotracheal tube applications.

An endotracheal tube is a specific type of tracheal tube that is nearly always inserted through the mouth (orotracheal) or nose (nasotracheal), and is a catheter that is inserted into the trachea for the primary purpose of establishing and maintaining a patent airway and to ensure the adequate exchange of oxygen and carbon dioxide. Tracheal intubation, usually simply referred to as intubaton, is the placement of a flexible catheter, e.g. plastic tube, into the trachea (windpipe) to maintain an open airway (or sometimes to serve as a conduit through which to administer certain drugs). It is frequently performed in critically injured, ill, or anesthetized patients to facilitate ventilation of the lungs, including mechanical ventilation, and to prevent the possibility of asphyxiation or airway obstruction.

Endotracheal tubes used for intubation can often be inserted incorrectly, particularly in traumatic scenarios. See Katz, S H; Falk, J L (2001). "Misplaced endotracheal tubes by paramedics in an urban emergency medical services system" (PDF). *Ann Emerg Med.* 37 (1): 32-7. See also Jones, J H; Murphy, M P; Dickson, R L; Somerville G G; Brizendine, E J (2004) "Emergency Physician Verified Out-of-Hospital Intubation: Miss Rates by Paramedics" *Aca-*

*demic Emergency Medicine,* 11(6): 707-9. In the prehospital setting, the incidence of unrecognized esophageal intubation has been reported to be as high as 1.8-2.0%, see Shea S R, MacDonald J R, Gruzinski G: "Prehospital endotracheal tube airway or esophageal gastric tube airway: A critical comparison" Ann Emerg Med 1985; 14:102-112.

There is a significant need for validation of proper endotracheal intubation. The position of the American College of Emergency Physicians, revised in 2016, states that confirmation of proper endotracheal tube placement should be completed in all patients at the time of initial intubation both in the hospital and out-of-hospital settings. Physical examination methods such as auscultation of chest and epigastrium, visualization of thoracic movement, and fogging in the tube are deemed not sufficiently reliable to confirm endotracheal tube placement. Similarly, pulse oximetry and chest radiography are not reliable as sole techniques to determine endotracheal tube location.

During intubation, direct visualization of the endotracheal tube passing through the vocal cords into the trachea, especially with the use of a videolaryngoscope, has been deemed to constitute firm evidence of correct tube placement, but additional techniques should be used as objective findings to confirm proper endotracheal tube position. The use of an end-tidal carbon dioxide detector (i.e., continuous waveform capnography, colorimetric and non-waveform capnography) has been proposed to evaluate and confirm endotracheal tube position in patients who have adequate tissue perfusion. However existing esophageal detector devices are deemed not as reliable as the various forms of capnography for the verification of endotracheal tube placement. Further, for patients in cardiac arrest and for those with markedly decreased perfusion, both continuous and non-waveform capnography may be less accurate. In these situations, if capnography is inconclusive, other methods of confirmation are desirable.

Ultrasound imaging may be used to reliably confirm endotracheal tube placement. However, this must be performed by someone who is experienced in this technique, and is not a practical real time solution in most applications. For background see Birmingham P K, Cheney F W, Ward R J: Esophageal intubation: A review of detection techniques. Anesth Analg 1986; 65:886-91; and Standards for Basic Anesthetic Monitoring, American Society of Anesthesiologists (last amended October 23), Directory of Members, 1996; 1998:438-9

There remains a need for a simple effective, efficient method and an apparatus for aspiration detection in respiratory assist device patients and for intubation verification of endotracheal tubes which can yield a reduction of morbidity and mortality of patients.

SUMMARY OF THE INVENTION

One aspect of this invention is directed to an integrated multimodal colorimetric based aspiration detection and intubation placement verification system for an endotracheal tube including a housing configured to be coupled to the endotracheal tube whereby patient exhalation can flow through an internal passage of the housing, and colorimetric based sensors within the housing are configured to come into contact with the patient exhalation, where the colorimetric based sensors are visible from the exterior of the housing, and wherein the colorimetric sensors include a Carbon Dioxide (CO2) sensor and at least one of i) a sensor for a first gastric acid, ii) a sensor for a second gastric acid different from the first gastric acid, and iii) PH sensor.

The term integrated within the meaning of the present invention defines that the system is found in a single unit, namely mounted within a single housing.

The phrase "multimodal colorimetric based" within the meaning of the specification references a plurality of distinct color changing based sensors, wherein the distinct sensors are directed to measuring or detecting distinct parameters.

One aspect of this invention is directed to an integrated multimodal colorimetric based aspiration detection system for a respiratory device including a housing configured to be coupled to the respiratory device whereby patient exhalation can flow through an internal passage of the housing; and colorimetric based sensors within the housing and configured to come into contact with the patient exhalation, where the colorimetric based sensors are visible from the exterior of the housing, and wherein the colorimetric sensors includes at least two of i) a CO2 sensor, ii) a sensor for a first gastric acid, iii) a sensor for a second gastric acid different from the first gastric acid, and iv) a PH sensor.

One aspect of this invention is directed to a colorimetric based aspiration detection system for a respiratory device comprising a housing configured to be coupled to the respiratory device whereby patient exhalation can flow through an internal passage of the housing, and at least one colorimetric based sensors within the housing and configured to come into contact with the patient exhalation, where each of the colorimetric based sensors are visible from the exterior of the housing, and wherein the colorimetric sensors includes at least a colorimetric sensor which senses butyric acid.

One aspect of the present invention provides a method of aspiration detection and intubation placement verification for an endotracheal tube comprising the steps of: Attempting to intubate the patient with an endotracheal tube; Providing an integrated multimodal colorimetric based aspiration detection and intubation placement verification system for an endotracheal tube having a housing and colorimetric based sensors within the housing, wherein the colorimetric sensors includes a CO2 sensor and at least one of i) a sensor for a first gastric acid, ii) a sensor for a second gastric acid different from the first gastric acid, and iii) a PH sensor; Coupling the housing to the endotracheal tube whereby patient exhalation can flow through an internal passage of the housing, wherein the colorimetric based sensors within the housing come into contact with the patient exhalation; and Visualizing the colorimetric based sensors from the exterior of the housing after they have come into contact with patient exhalation to detect aspiration and to verify intubation placement.

The features that characterize the present invention are pointed out with particularity in the claims which are part of this disclosure. These and other features of the invention, its operating advantages and the specific objects obtained by its use will be more fully understood from the following detailed description in connection with the attached figures.

BRIEF DESCRIPTION OF THE FIGURES

FIG. 1A is a schematic sectional view of a subject illustrating swallowing;

FIG. 1B is a schematic sectional view of a subject illustrating aspiration;

FIGS. 2 and 3 are sectional views of an integrated multimodal colorimetric based aspiration detection and intubation placement verification system for an endotracheal tube according to one embodiment of the present invention;

DESCRIPTION OF THE PREFERRED EMBODIMENTS

Figure 4:
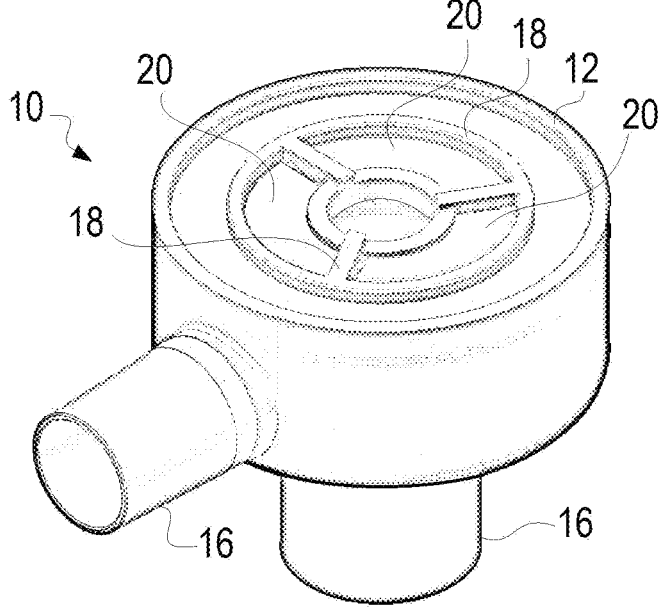
FIG. 4 is a perspective view of an integrated multimodal colorimetric based aspiration detection and intubation placement verification system for an endotracheal tube according to an alternative embodiment of the present invention.

FIGS. 2 and 3 show an integrated multimodal colorimetric based aspiration detection and intubation placement verification system 10 for an endotracheal tube including a housing 12 configured to be coupled to the endotracheal tube, such as to a bag valve mask, via inlet/outlet couplings 16. As noted above, the system 10 is references as integrated because the system 10 includes multiple distinct sensors 20 found in a single housing 12. The present system 10 is disclosed in connection with endotracheal tubes but is also applicable for coupling to a variety of respiratory assist devices including in the nasal cannula and masks of ventilation systems and also in CPAP devices and Bipap devices.

The system 10 for an endotracheal tube of the present invention may be coupled to an endotracheal tube through a bag mask valve. A bag valve mask, abbreviated to BVM and sometimes known by the proprietary name AMBU bag or generically as a manual resuscitator or "self-inflating bag", is a hand-held device commonly used to provide positive pressure ventilation to patients who are not breathing or not breathing adequately. The device is a required part of resuscitation kits for trained professionals in out-of-hospital settings (such as ambulance crews) and is also frequently used in hospitals as part of standard equipment found on a crash cart, in emergency rooms or other critical care settings.

The housing 12 of the integrated multimodal colorimetric based aspiration detection and intubation placement verification system 10 is configured whereby patient exhalation can flow through an internal passage of the housing 12 through a coupling 16 to a central chamber 14 and into contact with the sensors 20.

As shown in FIGS. 2 and 3, the inlet/outlet couplings 16 are formed as conventional fluid couplings to facilitate coupling the system 10 to an endotracheal tube or to other respiratory assist device. The inlet coupling 16 has an internal passage that leads to the central chamber 14 to which four distinct colorimetric sensors 20 are mounted within frames 18 and the outlet coupling 16 leads from the central chamber 14. The phrase "multimodal colorimetric based" within the meaning of the specification references a plurality or series of distinct color changing based sensors 20, wherein the distinct sensors are directed to measuring or detecting distinct parameters as detailed below.

Figure 5:
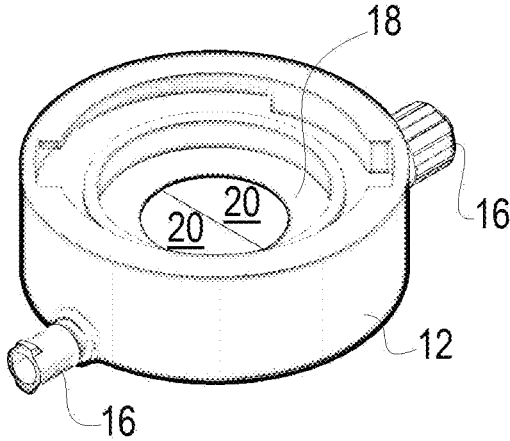
FIG. 5 is a perspective view of an integrated multimodal colorimetric based aspiration detection and intubation placement verification system for an endotracheal tube according to an alternative embodiment of the present invention.

The housing 12 could take many configurations. Conventional configurations include with the inlet/outlet couplings 16 aligned on opposite sides of the disc shaped central chamber 14, as shown in FIG. 5, or at a right angle or coming in the side and out the bottom as shown. It should be readily apparent that the illustrated embodiment of FIGS. 2-3 is only representative. The housing 12 itself is preferably formed of opaque material to minimize ambient light effecting the colorimetric sensors. Any color for the housing 12 is acceptable as long as the shading of the colorimetric sensors 20 is easily discernable.

Four distinct colorimetric based sensors 20 are mounted within the housing 12 within frames 18 and configured to come into contact with the patient exhalation. Colorimetric sensors or detectors are well established and are formed to indicate the presence of a target chemical through a chemical reaction that results in a color change. The distinct colorimetric sensors 20 of the system 10 of FIGS. 2-3 include a $CO_2$ colorimetric sensor 20, an HCL colorimetric sensor 20, a butyric acid colorimetric sensor 20, and PH colorimetric sensor 20.

The colorimetric sensors 20 are formed as a substrate, generally filter paper, impregnated with an indicator that visibly changes color via a chemical reaction in the presence of a present amount of the sensed target substrate. See for example Johnson Test Paper, CBRNE Tech Index (http://www.cbrnetechindex.com/Chemical-Detection/Technology-CD/Colorimetric-CD-T), and Millipore Sigma. For the purpose of the present invention the colorimetric sensors will exhibit a color change generally in less than 2 seconds when exposed to the parameter of interest. For example, the colorimetric paper from Johnson Test paper forming the HCL sensor changes color from blue to pink in the presence of HCl, with the sensitivity of the paper specified to be 0.5 ppm.

Regarding the $CO_2$ colorimetric sensor 20, colorimetric $CO_2$ sensors or detectors are generally known and have been used to verify proper endotracheal (ET) tube placement and are currently one of the accepted methods of verification. See for example the NELLCOR™ adult/pediatric colorimetric $CO_2$ detector and see generally U.S. Pat. Nos. 4,790,327; 4,928,687; 4,994,117; 5,005,572; 5,166,075; 5,179,002; 5,846,836, 5,965,061 and 6,502,573, which are incorporated herein by reference.

As discussed above, a critical step in the intubation of a patient is a determination that the breathing tube or intubation tube or endotracheal tube is placed in the trachea and not in the esophagus. If the tube is in the esophagus, there is no return of $CO_2$ from a patient's breath. If the tube is in the trachea, $CO_2$ will be present up to about five percent concentration. Since it is common in emergency situations for less highly skilled technicians to apply endotracheal tubes attached to a cardiopulmonary resuscitator (CPR) to a patient's airway, it is important to confirm the proper placement. The $CO_2$ sensor 20 of system 10 communicating with an endotracheal tube of the invention serves this purpose.

The hydrochloric acid (HCL) sensor 20 is for measuring HCL concentrations of select samples of the patient exhalation. HCl is the primary acid found in the stomach. Assuming the endotracheal tube has been properly placed, as will be evidenced by the triggered $CO_2$ sensor 20, the HCL sensor 20 activation (or trigger) is used for detecting aspiration of the patient. When the endotracheal tube is not properly placed the $CO_2$ senser will not verify the placement, and the HCL sensor 20 will be triggered giving an active visual indication of improper placement.

A key aspect of the present invention is the provision of a butyric acid sensor 20. Butyric acid is also known under the systematic name butanoic acid and is responsible for the stench of vomit. Thus, assuming the endotracheal tube has been properly placed, as will be evidenced by activated $CO_2$ sensor 20, the butyric acid sensor 20 is also used for detecting aspiration of the patient. When the endotracheal tube is not properly placed the $CO_2$ senser will not verify the placement, and the butyric acid sensor 20 will be triggered giving an active visual indication of improper placement.

The HCL sensor 20 and the butyric acid sensor 20 operate on different parameters to achieve the same purpose. In practice it is expected that there will be some situations in which the HCL sensor 20 operates faster at detecting aspiration than the butyric acid sensor 20, and vice versa. The faster detection of one gastric acid over the other may have population dependent parameters, however including both within the system 10 improves response times. In addition to faster response times with two distinct gastric acid sensors 20 there is a possibility that one of the gastric acid sensor 20 sensors is not triggered in an aspiration event and having the second distinct gastric acid sensor 20 essentially eliminates (or significantly further minimizes) undetected aspirations.

The fourth sensor 20 is a PH colorimetric sensor 20 which will effectively respond to the low PH of gastric acids. The normal pH range for stomach acid is between 1.5 and 3.5. The trigger point of the PH sensor 20 may be selected within a range of intragastric PH ranges for humans. See *pH dependence of add secretion and gastrin release in normal and ulcer subjects*. Walsh J H, Richardson C T, Fordtran J S *J Clin Invest* 1975 March; 55(3):462-8. One class of PH colorimetric sensor 20 is a graphene oxide based sensor that exhibits distinctive color response. See "Efficient Colorimetric pH Sensor Based on Responsive Polymer—Quantum Dot Integrated Graphene Oxide", Kwanyeol Paek, Hyunseung Yang, Junhyuk Lee, Junwoo Park, and Bumjoon J. Kim *ACS Nano* 2014 8 (3), 2848-2856 DOI: 10.1021/nn406657b.

When using four colorimetric sensors 20 in frames 18, four 90 degree arcuate segment frames 18 as generally shown in FIGS. 2-3 is effective. Other positions and arrangements are also possible. A clear cover (not shown) can be added over the top of the sensors 20 if desired.

An alternative version of the invention is shown in FIG. 4 in which three colorimetric sensors 20 are present in the system 10. Specifically, the distinct colorimetric sensors 20 of this system 10 include an HCL colorimetric sensor 20, a butyric acid colorimetric sensor 20, and PH colorimetric sensor 20, and this system 10 design is useful where CO2 monitoring is not needed in the device. The arrangement shown in the system 10 of FIG. 3 works for any combination of three colorimetric sensors 20. For example, the distinct colorimetric sensors 20 in an alternative system 10 embodiment includes a CO2 colorimetric sensor 20, an HCL colorimetric sensor 20, and a butyric acid colorimetric sensor 20, and this could be used where PH measurements are not deemed critical. Further, the distinct colorimetric sensors 20 in an alternative system 10 embodiment includes an CO2 colorimetric sensor 20, a PH sensor 20, and one gastric acid sensor 20 namely one of an HCL colorimetric sensor 20 and a butyric acid colorimetric sensor 20, and this could be used for populations in which either the HCL colorimetric sensor 20 or a butyric acid colorimetric sensor 20 represents dominant response times.

An alternative version of the invention is shown in FIG. 5 in which the system 10 includes two colorimetric sensors 10 (shown with a transparent cover removed) are present in a slightly distinct housing 12. The housing 10 uses aligned inlet/outlet couplings 16.

Returning to the embodiment of FIGS. 2-3, consider that intubation of a patient in the emergency room is often verified only by checking for lung sounds after bagging the patient with a bag-mask apparatus. This is not a fool-proof method, and if the endotracheal tube ends up in the esophagus, pumping air into the patient's stomach can lead to additional problems. Another problem frequently associated with emergent intubations is aspiration of gastric contents. This is more common in trauma patients presenting to the emergency room, than a patient being intubated electively. Often it remains undetected until the patient presents with features of pneumonia or fibrosis. Prevention of aspiration before it occurs, or treatment as soon as it is detected is crucial.

The integrated multi-modal colorimetric sensor system 10 of the invention includes sensors 20 formed of colorimetric pH paper, colorimetric HCl paper, colorimetric butyric acid paper and colorimetric CO2 paper. The system 10 is to be attached to the bag-mask apparatus so that exhaled air comes in contact with it. Air exhaled from the lungs should contain CO2; this will cause the colorimetric CO2 paper to be triggered and tochange color if the endotracheal tube is properly positioned. In addition to this, should acidic vapors be present in exhaled air from regurgitation, the pH paper, the colorimetric HCl papers and the colormetric butyric acid paper will change color, alerting the doctors and nurses to possible aspiration.

While EtCO2 detectors already exist, this system 10 is different in that it provides an extra layer of confirmation of placement along with the ability to detect aspiration. If the tube is in the esophagus, the pH paper, the HCl paper and/or the butyric acid paper should change color.

This system 10 is connected to the AMBU bag while ventilating patients and allows instant confirmation of correct placement of the endotracheal tube while also checking if aspiration has occurred by checking gaseous content of exhaled air. The system 10 is particularly useful in trauma patients.

As detailed above the present method can be described as follows: a method of aspiration detection and intubation placement verification for an endotracheal tube comprising the steps of: Attempting to intubate the patient with an endotracheal tube; Providing an integrated multimodal colorimetric based aspiration detection and intubation placement verification system 10 for an endotracheal tube having a housing 12 and colorimetric based sensors 20 within the housing 12, wherein the colorimetric sensors 20 includes a CO2 sensor 20 and at least one of i) a sensor 20 for a first gastric acid, ii) a sensor 20 for a second gastric acid different from the first gastric acid, and iii) a PH sensor 20; Coupling the housing 12 to the endotracheal tube whereby patient exhalation can flow through an internal passage of the housing, wherein the colorimetric based sensors 20 within the housing 12 come into contact with the patient exhalation; and Visualizing the colorimetric based sensors 20 from the exterior of the housing 12 after they have come into contact with patient exhalation to detect aspiration and to verify intubation placement.

The phrase "patient exhalation" in this application and in this context should be viewed as broader than patient respiration, as if the endotracheal tube is in the esophagus the gas flow though the coupled device of the invention is not conventional patient respiratory exhalation due to the tube misplacement. The present invention will promptly alert the practitioners of any such erroneous placement by a combination of no response/triggering or activation from the CO2 sensor 20 (indicating misplacement) coupled with the detection of the low PH and gastric acid from the remaining sensors 20.

While the invention has been shown in several particular embodiments it should be clear that various modifications may be made to the present invention without departing from the spirit and scope thereof. The scope of the present invention is defined by the appended claims and equivalents thereto.

What is claimed is:

1. An integrated multimodal colorimetric based aspiration detection and intubation placement verification system for an endotracheal tube comprising:

a) A housing having an inlet coupling and an outlet coupling coupled directly to a central chamber, wherein the inlet coupling is configured to be coupled to the endotracheal tube whereby patient respiratory exhalation can flow through a valveless internal passage of the housing formed by the inlet coupling the central chamber and the outlet coupling;

b) Colorimetric based sensors within the housing and configured to come into contact with the patient exhalation within the central chamber, where the colorimetric based sensors are visible from the exterior of the housing, and wherein the colorimetric sensors includes a CO2 sensor and at least one of i) a sensor for a first gastric acid, ii) a sensor for a second gastric acid different from the first gastric acid, and iii) a PH sensor.

2. The integrated multimodal colorimetric based aspiration detection and intubation placement verification system according to claim 1, wherein the colorimetric sensors includes both a sensor for a first gastric acid and a sensor for a second gastric acid different from the first gastric acid.

3. The integrated multimodal colorimetric based aspiration detection and intubation placement verification system according to claim 2, wherein one colorimetric sensor senses butyric acid.

4. The integrated multimodal colorimetric based aspiration detection and intubation placement verification system according to claim 3, wherein one colorimetric sensor senses hydrochloric acid, and wherein the central chamber is a disc shaped central chamber.

5. The integrated multimodal colorimetric based aspiration detection and intubation placement verification system according to claim 4, wherein one colorimetric sensor senses PH.

6. The integrated multimodal colorimetric based aspiration detection and intubation placement verification system according to claim 1, wherein the central chamber is a disc shaped central chamber and wherein one colorimetric sensor senses butyric acid and is in a frame coupled to the disc shaped central chamber.

7. The integrated multimodal colorimetric based aspiration detection and intubation placement verification system according to claim 2, wherein the central chamber is a disc shaped central chamber and wherein one colorimetric sensor senses PH and is in a frame coupled to the disc shaped central chamber.

8. An integrated multimodal colorimetric based aspiration detection system for a respiratory device comprising:

a) A housing having an inlet coupling and an outlet coupling coupled directly to a disc shaped central chamber, wherein the inlet coupling is configured to be coupled to the respiratory device whereby patient respiratory exhalation can flow through a valveless internal passage passage of the housing formed by the inlet coupling the central chamber and the outlet coupling;

b) Colorimetric based sensors within the housing and configured to come into contact with the patient exhalation within the disc shaped central chamber, where the colorimetric based sensors are visible from the exterior of the housing, and wherein the colorimetric sensors includes at least two of i) a CO2 sensor, ii) a sensor for a first gastric acid, iii) a sensor for a second gastric acid different from the first gastric acid, and iv) a PH sensor.

9. The integrated multimodal colorimetric based aspiration detection system according to claim 8, wherein the colorimetric sensors includes both a sensor for a first gastric acid and a sensor for a second gastric acid different from the first gastric acid.

10. The integrated multimodal colorimetric based aspiration detection system according to claim 9, wherein one colorimetric sensor senses butyric acid.

11. The integrated multimodal colorimetric based aspiration detection system according to claim 10, wherein one colorimetric sensor senses hydrochloric acid.

12. The integrated multimodal colorimetric based aspiration detection system according to claim 11, wherein one colorimetric sensor senses PH.

13. The integrated multimodal colorimetric based aspiration detection system according to claim 8, wherein one colorimetric sensor senses butyric acid.

14. The integrated multimodal colorimetric based aspiration detection system according to claim 13, wherein one colorimetric sensor senses PH.

15. The integrated multimodal colorimetric based aspiration detection system according to claim 14, wherein one colorimetric sensor senses CO2.

16. A colorimetric based aspiration detection system for a respiratory device comprising:

a) A housing having an inlet coupling and an outlet coupling coupled directly to a disc shaped central chamber, wherein the inlet coupling is configured to be coupled to the respiratory device whereby patient respiratory exhalation can flow through a valveless internal passage passage of the housing formed by the inlet coupling the central chamber and the outlet coupling;

b) At least one colorimetric based sensors within the housing and configured to come into contact with the patient exhalation within the disc shaped central chamber, where each of the colorimetric based sensors are visible from the exterior of the housing, and wherein the colorimetric sensors includes at least a colorimetric sensor which senses butyric acid.

17. The colorimetric based aspiration detection system for a respiratory device according to claim 16, wherein one colorimetric sensor senses CO2.

18. A method of aspiration detection and intubation placement verification for an endotracheal tube comprising the steps of:

a) Attempting to intubate the patient with an endotracheal tube;

b) Providing an integrated multimodal colorimetric based aspiration detection and intubation placement verification system for an endotracheal tube having a housing having an inlet coupling and an outlet coupling coupled directly to a disc shaped central chamber, and colorimetric based sensors within the housing, wherein the colorimetric sensors includes a CO2 sensor and at least one of i) a sensor for a first gastric acid, ii) a sensor for a second gastric acid different from the first gastric acid, and iii) a PH sensor;

c) Coupling the inlet coupling of the housing to the endotracheal tube whereby patient exhalation can flow through a valveless internal passage passage of the housing formed by the inlet coupling the central chamber and the outlet coupling, wherein the colorimetric based sensors within the housing come into contact with the patient exhalation within the disc shaped central chamber; and d) Visualizing the colorimetric based sensors from the exterior of the housing after they have come into contact with patient exhalation to detect aspiration and
to verify intubation placement.

19. The method of aspiration detection and intubation
placement verification for an endotracheal tube according to
claim 18, wherein the detection of patient aspiration
includes the detection of butyric acid in the patient respiratory exhalation.

20. The method of aspiration detection and intubation
placement verification for an endotracheal tube according to
claim 19, wherein the intubation placement verification for
an endotracheal tube includes the detection of CO2 in the
patient respiratory exhalation.

* * * * *